United States Patent [19]

Williams

[11] Patent Number: 4,666,308
[45] Date of Patent: May 19, 1987

[54] METHOD AND APPARATUS FOR NON-DESTRUCTIVE TESTING USING ACOUSTIC-OPTIC LASER PROBE

[75] Inventor: Clayton C. Williams, Katonah, N.Y.

[73] Assignee: Stanford University, Stanford, Calif.

[21] Appl. No.: 666,354

[22] Filed: Oct. 30, 1984

[51] Int. Cl.[4] ............................................. G01N 21/00
[52] U.S. Cl. ...................................... 356/432; 350/358
[58] Field of Search ................. 356/432, 433; 350/358; 73/643

[56] References Cited

U.S. PATENT DOCUMENTS

| | | | |
|---|---|---|---|
| 3,424,906 | 1/1969 | Korpel | 350/358 |
| 3,431,504 | 3/1969 | Adler | 350/358 |
| 3,948,345 | 4/1976 | Rosencwaig | 356/432 |
| 4,046,477 | 9/1977 | Kaule | 73/643 |
| 4,137,991 | 2/1979 | Melcher et al. | 73/643 |
| 4,255,971 | 3/1981 | Rosencwaig | 73/643 |
| 4,267,732 | 5/1981 | Quate | 73/643 |

Primary Examiner—R. A. Rosenberger
Attorney, Agent, or Firm—Flehr, Hohbach, Test, Albritton & Herbert

[57] ABSTRACT

Apparatus for non-destructively inspecting a material includes a housing for holding the material with a window in the housing for the transmission of a laser beam and a pressurized fluid within the housing in contact with the material. A first laser source generates a first beam at a first frequency, and the beam is directed through the window and onto said material. A second laser source generates a second beam at a second frequency, the second frequency being related to the first frequency whereby Bragg scattering of the second beam is realized in the pressurized fluid. The second beam is directed through the window and onto said material, and the Bragg scattered second beam is detected.

7 Claims, 4 Drawing Figures

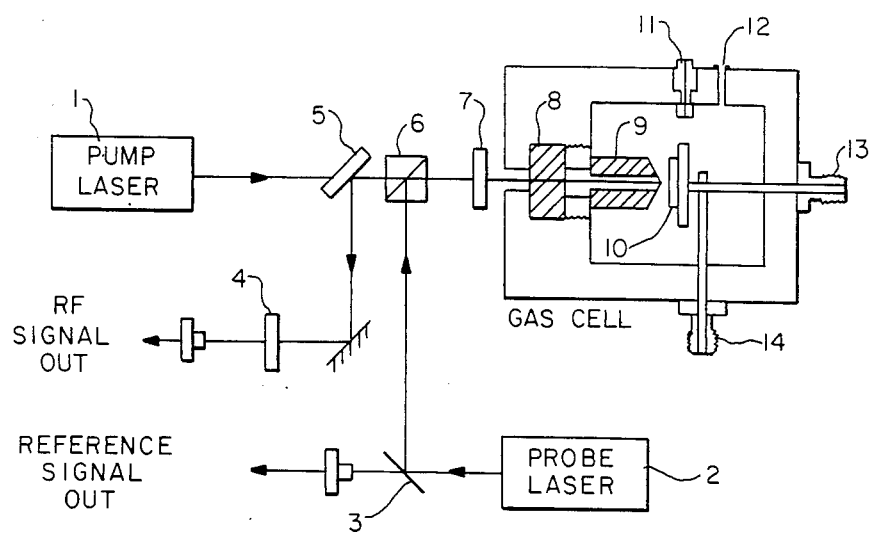
FIG.—1
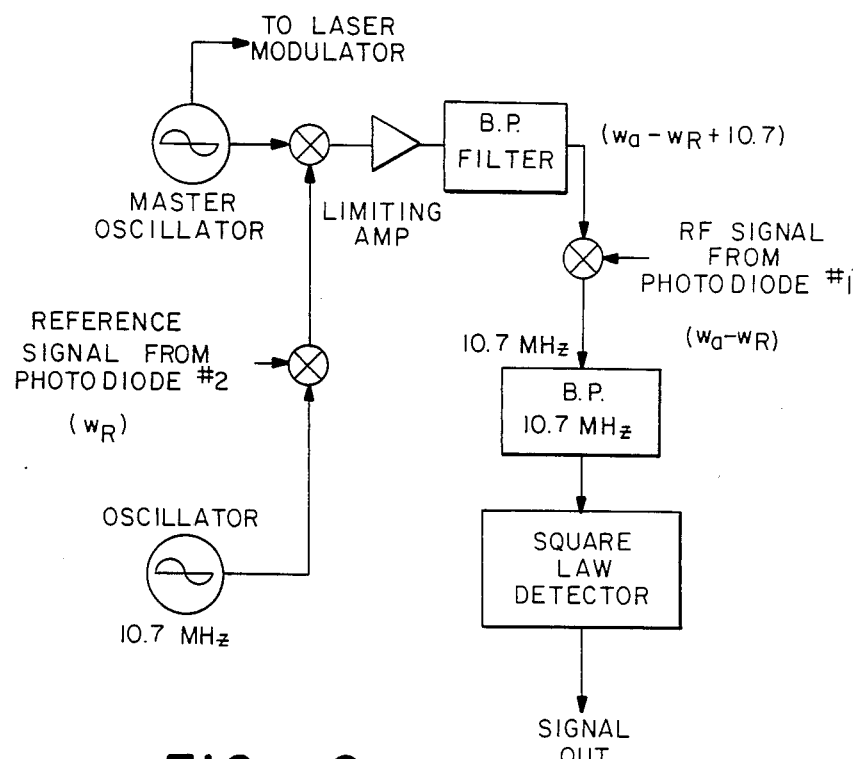
FIG.—2

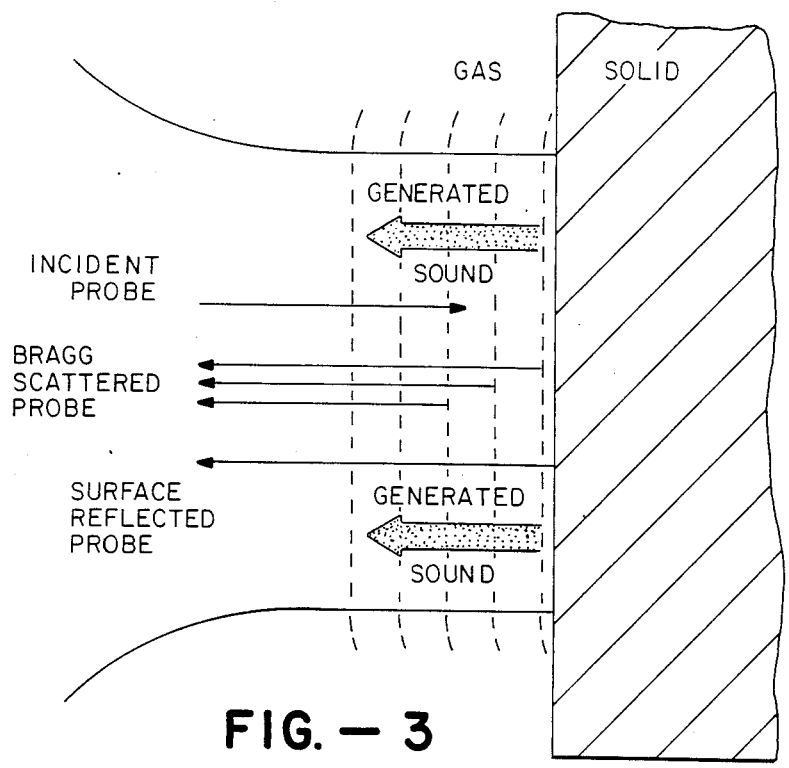
FIG. — 3
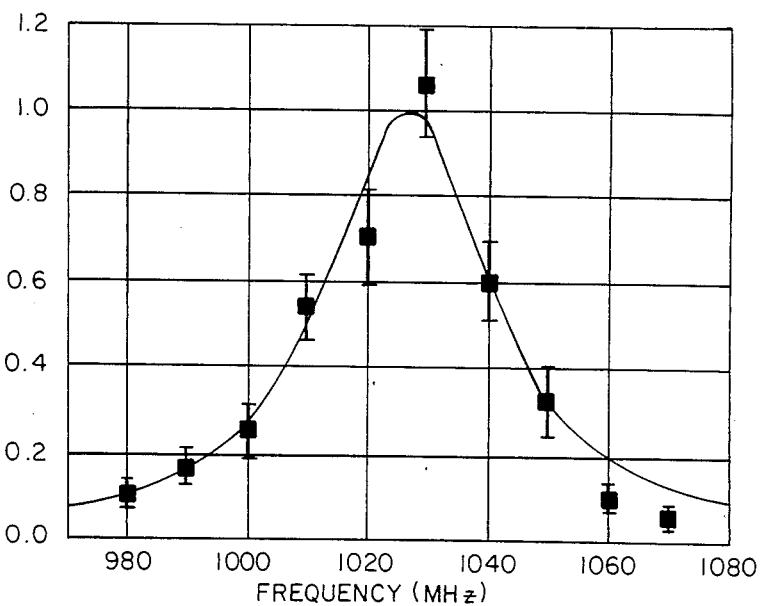
FIG. — 4

METHOD AND APPARATUS FOR NON-DESTRUCTIVE TESTING USING ACOUSTIC-OPTIC LASER PROBE

The U.S. Government has rights in the disclosed invention pursuant to U.S. Air Force Contract No. AFOSR-82-0248.

This invention relates generally to the non-destructive testing of materials, and more particularly the invention relates to use of an acousto-optic laser probe in such testing.

Photoacoustic and thermoacoustic spectroscopy is known in the prior art. See for example U.S. Pat. No. 4,255,971 for "Thermoacoustic Microscopy" and U.S. Pat. No. 4,267,732 for "Acoustic Microscope and Method". Basically, a sample material is heated by a suitable electromagnetic energy source, such as a laser, and the heated body generates acoustic waves at the frequency of the modulated electromagnetic energy. The amplitude of the acoustic wave is a function of the sample material properties. The prior art employs piezoelectric transducer means to detect the acoustic waves generated by the test sample.

The present invention is directed to use of an acousto-optic probe to detect the acoustic waves in a fluid caused by photothermal energy in a sample emersed in the fluid. More particularly, a light from the probe interacts with the acoustic waves in the fluid. By selecting the wavelength of the light to be twice the wavelength of the acoustic wave in the fluid, colinear Bragg scattering or reflection of the light results. The reflected wave has a frequency which is the sum of the input frequency and the frequency of the acoustic wave in the fluid. This reflection is then detected by mixing the Bragg scattered reflection with the light reflected from the sample, and the difference or acoustic frequency is then obtained.

Importantly, the probe can be operated at frequencies near one gigahertz, therefore a submicron spatial resolution can be realized.

Accordingly, an object of the invention is an improved method of non-destructive testing of a sample using thermoacoustic probes.

Another object of the invention is apparatus for thermoacoustic examination of a material with improved spatial resolution.

A feature of the invention is the use of Bragg scattering of an optical wave by acoustic waves in a fluid in contact with an energized sample material.

The invention and objects and features thereof will be more readily apparent from the following detailed description and appended claims when taken with the drawing, in which:

FIG. 1 is a schematic diagram of apparatus in accordance with one embodiment of the invention.

FIG. 2 is a functional block diagram of heterodyne detection apparatus useful with the embodiment of FIG. 1.

FIG. 3 is a schematic illustration of wave patterns in the apparatus of FIG. 1.

FIG. 4 is a plot of relative Bragg reflectivity versus pump modulation frequency in the embodiment of FIG. 1.

A schematic diagram of test apparatus in accordance with one embodiment of the invention is shown in FIG. 1. This is an arrangement used for detecting photothermally generated sound. A modulated pump laser is focused by an optical microscope objective inside the gas cell to a diffraction limited spot on the sample surface 10. A probe laser 2 is also focused at the same location. The modulated pump laser photothermally generates sound which propagates into the sample as well as into the gas. The amount of sound generated depends upon the properties of the sample. The probe laser is reflected at the sample surface with no shift in frequency, as well as reflected and frequency shifted by the sound wave propagating in the gas. The quarter wave plate outside the cell allows the reflected light to be transmitted through the polarizing beamsplitter, and is focused onto a fast photodetector. The photodetector is isolated from the pump laser by a narrowband spike filter placed in front of the detector. The sample is positioned for focus and translated by two micrometers from outside the gas cell. A reference signal at the frequency of the axial mode spacing of the probe laser ($\omega_r$) is detected in a second photodetector.

To avoid the problems of RF interference that occur when detecting at the modulation frequency of the pump laser ($\omega_a$), the two longitudinal modes of the HeNe probe laser are used to mix the heterodyne signal to a frquency other than that of the acoustic wave. This is accomplished by optically mixing the Bragg shifted signal from one axial mode ($\omega_0 + \omega_a$) with the unshifted frequency of the second axial mode ($\omega_0 + \omega_r$). The result is a heterodyne signal at the difference between the acoustic frequency and the axial mode spacing ($\omega_a - \omega_r$). Electronically mixing the reference signal ($\omega_r$) with the master oscillator ($\omega_a$) and adding a 10.7 MHz local oscillator generates an RF signal at ($\omega_a - \omega_r + 10.7$ MHz) which can then be used to mix the optical signal down to 10.7 MHz. It is then passed through a crystal filter with a 10 kHz bandwidth. The detection scheme can be seen in FIG. 2. The frequency dependence of the Bragg interaction was measured in the following way. A sapphire flat with a 1 GHz acoustic transducer on one side, and an amorphous carbon matching layer on the other was placed in the gas cell. It was positioned so that the incident light was focused onto the carbon layer where the acoustic power was incident from the sapphire. RF pulses were than sent to the transducer, generating acoustic power which propagated down the sapphire flat into the gas. The acoustic power in the gas then generated an acousto-optic signal which was measured. The frequency of the RF input was varied, and at each frequency, the insertion loss of the transducer was measured using a pulsed reflection technique. Also, the transmission factor from sapphire to the gas was calculated including the effects of the carbon matching layer. The measurement of the acousto-optic signal, made at each frequency, was then normalized by the proper transmission factor and insertion loss for that frequency. The experimental results are shown with the theoretical frequency dependence in FIG. 4, supra. There is good agreement between theory and experiment.

Following is a theoretical discussion of the operation of the apparatus. When sound propagates through a high density gas, the fluctuations in the local density cause a perturbation of the index of refraction. This perturbation of the dielectric constant causes a scattering of light which is incident upon the perturbed gas. Under proper phase matching conditions, i.e. the Bragg condition, the scattering can be significant. To calculate the efficiency of this interaction between the sound and incident light, we must first derive the photoelastic constant, which relates the condensation of the gas to the perturbation of the dielectric constant. We can derive the photoelastic constant for an ideal gas using the Lorentz-Lorenz formula $$\alpha_{pol} = \frac{3\epsilon_o(o-1)}{N(o+2)} \quad (1)$$

where $\alpha_{pol}$ is the mean polarizability of the atoms or molecules, $\epsilon_o$ is the permittivity of free space, o is the relative dielectric constant, and N is the number of atoms or molecules per unit volume. For a gas, where $(\epsilon-1)$ is much less than 1, it can be shown that $$(\epsilon - 1) \approx \frac{N\alpha_{pol}}{MW\epsilon_o \rho} \quad (2)$$

where MW is the molecular or atomic weight of the medium, and $\rho$ is the density. Taking the derivative of equation 2, we find that for a small change in density $\delta\rho$, the corresponding change in the relative dielectric constant $\delta\rho$ is given by $$\delta\epsilon = (\epsilon - 1)\frac{\delta\rho}{\rho o} = (\epsilon - 1)S \quad (3)$$

where $S=(\rho-\rho o)/\rho o$ is the acoustic condensation. When light propagates through the gas simultaneously with the sound, a nonlinear polarization wave is generated whose amplitude is proportional to the product of the acoustic and electromagnetic fields. This polarization wave radiates optical power at the sum and difference frequencies of the acoustic and optical waves. When the wavelength of the sound in the gas is one half that of the light, phase matching takes place for collinear propagation of the light and the sound. The incident light is back reflected from the sound wave. See FIG. 3.

The efficiency of the scattering can be called a "Reflectivity". Using Maxwell's equations to obtain the inhomogeneous wave equation, and the photoelastic relation, we can calculate the power reflectivity $\Gamma$ due to the sound wave in the gas. The result for the k vector matched case is given by $$\Gamma = \left[\frac{\pi(\epsilon-1)S_0}{2\alpha\lambda_o}\right]^2 \quad (4)$$

where $\epsilon$ is the relative dielectric constant of the gas, $S_o$ is the peak condensation in the gas, $\alpha$ is the attenuation constant of the gas, and $\lambda_o$ is the wavelength of the incident light in the gas.

As mentioned above, the Bragg interaction depends on k-vector matching of the incoming and reflected light fields with the acoustic field. It can be shown that the magnitude of the Bragg scattered field depends on the k-vector mismatch $\Delta\kappa$ according to $$|\sqrt{\Gamma}| \sim \left|\int_o^\infty e^{-\alpha z}e^{j\Delta kz}dz\right| = \left|\frac{1}{\sqrt{\alpha^2 + \Delta\kappa^2}}\right| \quad (5)$$

The signal is proportional to the power reflectivity, therefore $$P_{signal} \sim \Gamma = \left[\frac{\pi(\epsilon-1)S_0}{2\alpha\lambda_o}\right]^2 \left(\frac{1}{\alpha^2 + \Delta\kappa^2}\right) \quad (6)$$

where $\Delta\kappa=\kappa_o-\kappa_a+\kappa_s 2\kappa_o-\kappa_a$. In terms of frequency, $\Delta\kappa=(\omega-\omega_o)/V_a$, where $\omega_o$ is the acoustic frequency at which $\Delta\kappa$ is zero, and $V_a$ is the velocity of sound in the gas. As can be seen from equation 5, there is a fourier transform relationship between the spatial dependence of the acoustic wave and the frequency dependence of the Bragg interaction. Because the acoustic wave is exponentially damped, the frequency dependence is Lorentzian. The theoretically expected frequency dependence, with some experimental data taken, is shown in FIG. 4.

The efficiency of the Bragg scattering depends upon the pressure of the gas through the dielectric constant and the acoustic attenuation constant. These parameters of the gas depend upon the pressure in the following way.

$$(\epsilon-1)\sim\rho\sim.P_{gas} \quad (7)$$

$$\alpha\sim 1/P_{gas} \quad (8)$$

Substituting equations 7 and 8 into equation 4, we find that $$\Gamma\sim P_{gas}^4 S_0^2 \quad (9)$$

If we relate the reflectivity to the acoustic power density in the gas, we find that $$S_0^2 = 2I_a/\rho V_a^3 \quad (10)$$

where $$\rho\sim P_{gas} \quad (11)$$

and $$V_a\sim \text{constant} \quad (12)$$

Therefore, $\Gamma$ goes as the third power of the pressure of the gas for a given acoustic intensity $$\Gamma\sim P_{gas}3/a \quad (13)$$

We will now look at the sensitivity of this probe to acoustic power either photothermally generated, or transmitted from a solid to the gas. The incident probe beam of average power $P_o$ is reflected by the sound in the gas with power reflection coefficient $\Gamma$, and reflected from the sample surface with power reflection coefficient R. Both reflected components propagate collinearly back to the photodetector where they generate a heterodyne signal at the frequency of the acoustic wave in the gas. The optical heterodyne power is proportional to the product of the fields from these two reflections. The peak optical heterodyne power at frequency $(W_a)$ is given by $$P_{het} = 2\sqrt{RP_o}\sqrt{\Gamma P_o} = 2\sqrt{R}\sqrt{\Gamma}P_o \quad (14)$$

Conversion of the optical heterodyne power to an RF signal takes place in the photodetector. The peak heterodyne current is given by $$I_{het} = \alpha_r P_{het} \tag{15}$$

where $\alpha_r$ is the responsivity (amps/watt) of the photodetector. The average signal power into the load resistor is thus given by $$P_{signal} = \tfrac{1}{2} I^2_{het} R_1 = 2\alpha_r^2 R\Gamma P_o^2 R_1 \tag{16}$$

There are three sources which contribute noise to the signal as it is detected and amplified. They are shot noise, Johnson noise, and amplifier noise. The total noise power contributed by these three sources is given by $$P_{noise} = 4KTBF + 2e\alpha_r BR P_o R_1. \tag{17}$$

where K is the Boltzman's constant, T is the absolute temperature, B is the bandwidth, F is the noise figure of the preamplifier, E is the electron charge, $\alpha_r$ is the detector responsivity (A/W), $R_1$ is the load resistance, and $P_o$ is the average detected power. Thus the signal-to-noise ratio is given by $$\frac{S}{N} = \frac{2\alpha_r^2 R\Gamma P_o^2 R_l}{4KTBF + 2e\alpha_r BR P_o R_l} \tag{18}$$

SENSITIVITY TO BRAGG REFLECTIVITY

Rearranging equation 18, we can calculate the minimum reflectivity measurable for a given signal-to-noise ratio.

$$\Gamma = \left(\frac{S}{N}\right) \frac{(4KTBF + 2e\alpha_r BR P_o R_1)}{2\alpha_r^2 R P_o^2 R_1} \tag{19}$$

Under the following conditions,
B = 5 HZ (0.1 sec integration time)
F = 1.77 (2.5 db noise figure of preamplifier)
$\alpha_r = 0.33$ a/w (detector responsivity)
$P_o = 1.0$ mW (incident optical power)
R = 1 (sample reflectance)
$R_1 = 50\Omega$ (load resistance)
the minimum reflectivity detectable with a given signal-to-noise is $$\Gamma = \left(\frac{S}{N}\right)(1.5 \times 10^{-14}). \tag{20}$$

Therefore, a Bragg reflectivity of approximately $10^{-14}$ should be detectable with a signal-to-noise of one.

We can now relate the Bragg reflectivity to the acoustic power density to determine the sensitivity to acoustic power. Using equations 4 and 11, we obtain an expression for the reflectivity $\Gamma$ in terms of the acoustic intensity $1_a$.

$$\Gamma = \left[\frac{\pi(\epsilon - 1)}{2\alpha\lambda_o}\right]^2 \left(\frac{2I_a}{\rho V_a^3}\right) \tag{21}$$

Using values for argon gas at 100 atmospheres, $(\epsilon - 1) = 0.055$ $V_a \approx 323$ m/s $\rho = 160$ kg/m$^3$ $\alpha = 1.7 \times 10^5$ m$^{-1}$ $\lambda_o = 0.6328 \times 10^{-6}$ m the reflectivity is calculated in terms of the acoustic intensity.

$$\Gamma = (2.1 \times 10^{-10}) I_a \tag{22}$$

Using the results from equations 20 and 22, we can now calculate the minimum acoustic intensity measurable for a given signal-to-noise ratio.

$$I_a = (7.4 \times 10^{-5})(S/N) \tag{23}$$

For a signal-to-noise ratio of one, we should be able to detect less than $10^{-4}$ W/m$^2$ of acoustic power over an area of approximately 1 square micron. In this case, the total detected power is less than $10^{-16}$ Watts. The corresponding surface displacement under these conditions is less than $10^{-4}$ angstroms.

A measurement of the absolute sensitivity of the probe at 50 atmospheres was made using the acoustic flat mentioned above. In this experiment, the peak power of the input RF pulses, along with the insertion loss, was measured at the Bragg resonance frequency. This information allowed a determination of the total acoustic power in the sapphire flat. The acoustic spot size at the carbon matching layer was calculated numerically. Also, the transmission from the flat to the gas was calculated taking into account the effects of the matching layer. This information made possible the calculation of the absolute acoustic power density in the gas.

A measurement of the acousto-optic signal-to-noise ratio was then measured, along with the incident and detected optical power levels. Below are found the experimental and calculated data.
$P_{gas} = 50$ atmospheres
$P_o = 1.75$ mW
$R_{eff} = 0.04$
F = 1.77
B = 5 MHz
$R_1 = 50\Omega$ Using these values, the theory predicts that the minimum acoustic intensity detectable with a signal-to-noise of one is $$I_{amin} = 3.9 \times 10^3 W/m^2 \tag{24}$$

The measured minimum detectable acoustic intensity was $$I_{amin} = 5.5 \times 10^4 W/m^2 \tag{25}$$

This means that experimental results deviate from that predicted by theory by a factor of 14.1 in acoustic power.

One of the sources of the discrepancy between the predictions of theory and the experimental measurement is that the probe laser used in this experiment has two axial modes which are used to allow detection at a frequency other than the acoustic frequency. The theory assumed a single mode laser probe. Using a two mode probe laser reduces the expected sensitivity to acoustic power by a factor of 4. This leaves a discrepancy of a factor of 3.5. The source of this factor is presently uncertain.

Note that under these experimental conditions, the detection is Johnson noise limited. By using a probe laser modulated near the acoustic frequency, detection of the heterodyne power could be done at low frequencies. allowing for a large load resistance. The detection would then become shot noise limited. In this case, the sensitivity to acoustic power would increase by more than a factor of 30.

The dependence of the signal on pressure was measured in the following way. The signal power was measured while varying the gas pressure in the cell for constant input RF power. Since the transmission of acoustic power from the sapphire to the gas varies with gas pressure (the impedance of the gas is proportional to it's density), the signal was normalized by this transmission factor. The measured pressure dependence was $$P_{signal} \sim P_{gas} 2.5 \qquad (26)$$

over a pressure range of 26 to 66 atmospheres. The theory predicts that is should go as the third power of the gas pressure.

The primary application for this probe is to detect photoacoustically generated sound near 1 GHz. The reasons for this are the following. Although the sensitivity of this probe is comparable to displacement interferometry for detection of acoustic power transmitted through an object, its sensitivity to photoacoustically generated acoustic power at the surface of a solid is more than an order of magnitude greater than that of photodisplacement at frequencies near 1 GHz. This is due to the fact that the acoustic power thermally generated in the gas is much greater than the thermally generated power coupled from the solid to the gas via surface displacement. The second reason is that one dimensional theory predicts an inverse dependence upon the thermal conductivity for strongly absorbing solids. This means it may be possible to measure and spatially map thermal conductivities with high resolution. At frequencies near 1 GHz, the thermal wavelength in most solids is less than 1000 angstroms. The photothermal resolution would essentially be determined by the optical spot size. Some interesting candidates for study may be silicon and gallium arsenide devices which have been implanted or doped to modify their electrical conductivity with high spatial definition. The capability to measure the thermal conductivity on a microscopic scale may prove useful as a diagnostic tool in the processing of integrated circuits.

The non-destructive probe in accordance with the invention has particular applicability in inspecting semiconductor devices for material defects in the semiconductor bodies or in thin films such as silicon oxide thereon. In such applications the flaws will affect the thermoconductivity of illuminated surface areas as the laser beam is scanned thereacross, thereby changing the amplitude of the acoustic waves in the fluid environment.

Work relating to the invention is described in detail in applicant's thesis entitled "High Resolution Photoacoustic and Photothermal Imaging" dated June 1984 and submitted to the Department of Electrical Engineering, Stanford University, Palo Alto, Calif. The detection system is described in applicant's paper entitled "High Resolution Acoustic-Optic Laser Probe", Proceedings of the IEEE Ultrasonics Symposium, Oct. 31, 1983. The signal generation is described in applicant's paper entitled "High Resolution Photothermal Laser Probe", Applied Physics Letters 44 (12), June 15, 1984.

While the invention has been described with reference to a specific embodiment, the description is illustrative of the invention and not limiting the invention. Various modifications and applications may occur to those skilled in the art without departing from the true spirit and scope of the invention as defined by the appended claims.

What is claimed is:

1. Apparatus for non-destructively inspecting a material comprising
   a housing for holding said material and including window means in said housing for the transmission of an electromagnetic beam and including a fluid within said housing in contact with said material,
   a first electromagnetic source for generating a first electromagnetic beam modulated at a first frequency,
   means for directing said first electromagnetic beam through said window means and onto said material and generating acoustic waves in said fluid at said first frequency,
   a second electromagnetic source for generating a second electromagnetic beam at a second frequency, said second frequency being related to said first frequency whereby Bragg scattering of said second beam is realized in said fluid,
   means for directing said second electromagnetic beam through said window means and onto said material, and
   means for detecting said Bragg scattered second beam.

2. Apparatus as defined by claim 1 wherein said first electromagnetic source comprises a first laser for generating said first beam at a modulation frequency of $\omega_a$,
   said second electromagnetic source comprising a second laser for generating said second beam having one mode at a frequency of $\omega_o$,
   said Bragg scattered second beam having a frequency of $\omega_o + \omega_a$.

3. Apparatus as defined by claim 2 wherein said means for detecting heterodynes said reflected beam having frequency of $\omega_o + \omega_a$ with a signal at frequency $\omega_o$ to obtain a signal at frequency $\omega_a$.

4. Apparatus as defined by claim 2 wherein said second beam includes a second mode at frequency $\omega_o + \omega_r$, said detector means including a first detector for obtaining a signal at the frequency $\omega_r$ and a second detector for obtaining a signal at $\omega_a - \omega_r$.

5. Apparatus as defined by claim 4 wherein said means for detecting further includes means for mixing said signal at $\omega_r$ with a lower frequency signal $\omega_1$ and obtaining a signal frequency of $\omega_r + \omega_1$, means for mixing said frequency at $\omega_r + \omega_1$ with said $\omega_a$ signal and obtaining a signal at frequency of $\omega_a + \omega_r + \omega_1$, and mixer means for mixing said signal at $\omega_a + \omega_r + \omega_1$ with said detected signal at $\omega_a + \omega_r$ thereby obtaining a signal at $\omega_1$ which is indicative of said acoustic wave, $\omega_a$, in said fluid.

6. Apparatus as defined by claim 1 wherein said fluid is chosen from argon gas and argon liquid.

7. A method of non-destructive testing of material comprising the steps of
   placing said material in a fluid environment, energizing a surface of said material with a first electromagnetic wave modulated at freqiuency $\omega_a$ thereby generating acoustic waves in said fluid, directing a second electromagnetic wave at a frequency $\omega_o$ onto said surface, said frequency $\omega_o$ being related to said frequency $\omega_a$ whereby Bragg scattering and reflection of said second electromagnetic wave occurs in said fluid environment, and detecting the reflected second electromagnetic wave.